United States Patent
Neufeld et al.

[11] Patent Number: 5,869,117
[45] Date of Patent: Feb. 9, 1999

[54] IMMOBILIZED-CELL CARRAGEENAN BEAD PRODUCTION AND A BREWING PROCESS UTILIZING CARRAGEENAN BEAD IMMOBILIZED YEAST CELLS

[75] Inventors: Ronald James Neufeld, Beaconsfield, Canada; Denis J. C. M. Poncelet, Vandoeuvre, France; Sylvain D. J. M. Norton, London, Canada

[73] Assignee: Labatt Brewing Company Limited, London, Canada

[21] Appl. No.: 812,669

[22] Filed: Mar. 10, 1997

Related U.S. Application Data

[63] Continuation of Ser. No. 368,840, Jan. 5, 1995, abandoned.

[30] Foreign Application Priority Data

Oct. 6, 1994 [CA] Canada ................................. 2133789

[51] Int. Cl.$^6$ ............................ C12N 11/02; C12N 11/04
[52] U.S. Cl. .............................. 426/62; 426/16; 435/177; 435/182
[58] Field of Search ................................. 426/11, 16, 61; 435/177, 182

[56] References Cited

U.S. PATENT DOCUMENTS

| | | | |
|---|---|---|---|
| 4,647,536 | 3/1987 | Mosbach et al. | 435/177 |
| 4,698,224 | 10/1987 | Nakanishi et al. | 426/11 |
| 4,940,734 | 7/1990 | Ley et al. | 521/84.1 |
| 5,037,740 | 8/1991 | Tanaka et al. | 435/42 |
| 5,070,019 | 12/1991 | Hill | 435/178 |
| 5,079,011 | 1/1992 | Lommi et al. | 426/11 |
| 5,662,840 | 9/1997 | Thomas et al. | 264/12 |

FOREIGN PATENT DOCUMENTS

WO 90/05189  5/1990  WIPO.

OTHER PUBLICATIONS

Nagashima, et al., "Large–Scale Preparation of Calcium Alginate–Immobilized Yeast Cells and Its Application to Industrial Ethanol Production," *Methods in Enzymology* vol. 136 (1987), 394–405.

Nojima, et al., "Large–Scale Production of Photo–Cross–Linkable Resin–Immobilized Yeast and Its Application to Industrial Ethanol Production," *Methods in Enzymology* vol. 136 (1987), 380–394.

Tosa, et al., "Immobilization of Enzymes and Microbial Cells Using Carrageenan as Matrix," *Biotechnology and Bioengineering* vol. XXI (1979), 1697–1709.

(List continued on next page.)

*Primary Examiner*—Curtis E. Sherrer
*Attorney, Agent, or Firm*—Commarata & Grandinetti

[57] ABSTRACT

A process for immobilizing viable cells in gelled carrageenan beads comprises preparing an aqueous phase that is a mixture of a gellable concentration of un-gelled carrageenan, in an aqueous suspension of viable cells, in which the mixture's potassium concentration is low enough that the thermogellation temperature of the carrageenan in the suspension is below a temperature to which the viable cells are substantially thermosensitive. This is done at a first processing temperature that exceeds the thermogellation temperature of the carrageenan in that aqueous suspension, but which is below the temperature to which the cells are substantially thermosensitive. A mixture of the aqueous phase and a non-reactive food-grade oil phase is then prepared, and subjected to shear by passing it through a static mixer under flow-rate conditions selected to disperse the aqueous phase in the oil phase, such that a resulting emulsion has a selected droplet size distribution. Thereafter, the temperature of the resulting emulsion is decreased from the first processing temperature, to a second processing temperature which is below the thermogellation temperature of the carrageenan in the suspension. This results in the formation of polymer gel beads having the immobilized viable cells entrapped therein.

7 Claims, 3 Drawing Sheets

OTHER PUBLICATIONS

Ogbonna, et al., "Production of Micro–Gel Beads by a Rotating Disk Atomizer," *Journal of Fermentation and Bio–engineering* vol. 68, No. 1 (1989), 40–48.

Nakanishi, et al., "A new immobilized yeast reactor system for rapid production of beer," *EBC Congress* (1985) 331–338.

Nakanishi, et al., "A New Immobilized Yeast Reactor System for Rapid Production of Beer," *Rep. Res. Lab. Kirin Brew Co.* No. 29 (1986), 13–16.

Aivasidis, et al., "Continuous fermentation of alcohol–free beer with immobilized yeast in fluidized bed reactors," *Proc. Eur. Brew.* (1991) 569–576.

Dr. Klaus Breitenbücher, "Continuous Brewing with Immobilized Brewing Yeast," *Brew. Beverage Ind. Inl.* (1992), 28, 30 and 31.

Godia, et al., "Immobilized Cells; Behavior of Carrageenan Entrapped Yeast during Continuous Ethanol Fermentation," *Appl. Microbiol. Biotechnol.* (1987), 342–346.

J.H.T. Luong, "Cell Immobilization in K–Carrageenan for Ethanol Production," *Biotechnology and Bioengineering* vol. XXVII (1985), 1652–1661.

Nagashima, et al., "Continuous Ethanol Fermentation Using Immobilized Yeast Cells," *Biotechnology and Bioengineering* vol. XXVI (1984), 992–997.

Takata, et al., "Screening of Matrix Suitable for Immobilization of Microbial Cells," *Journal of Solid–Phase Biochemistry* vol. 2, No. 3, (1977) 225–236.

Nilsson, et al., "Entrapment of Microbial and Plant Cells in Beaded Polymers," *Methods in Enzymology* vol. 135 (1987), 222–223.

Audet, et al., "Two–phase Dispersion Process for the Production of Biopolymer Gel Beads: Effect of Various Parameters on Bead Size and Their Distribution," *Biochemistry* (Dec. 1989), 217–226.

Poncelet, et al., "Production of alginate beads by emulsification/internal gelation: I. Methodology," *Applied Microbiology and Biotechnology* (1992), 39–45.

Jukka Kronløf, "Immobilized yeast in continuous fermentation of beer," *VTT Publications* 167 (1994), 1–V/8.

IMMOBILIZED-CELL CARRAGEENAN BEAD PRODUCTION AND A BREWING PROCESS UTILIZING CARRAGEENAN BEAD IMMOBILIZED YEAST CELLS

This application is a continuation of application Ser. No. 08/368,840, filed Jan. 5, 1995, abandoned.

FIELD OF THE INVENTION

The present invention relates to the formation of carrageenan-beadimmobilized cells, especially yeast cells, and in particular to a process for the use of it in the production of alcohols through fermentation. The process is particularly advantageous for producing immobilized yeast cell beads for use in the production of ethanol, and especially in relation to the production of fermented beverages, such as wine or beer.

BACKGROUND OF THE INVENTION

Historically, wine fermentations were permitted to run their course, using only the diverse wild yeast strains that were indigenous to the fruit's surface. That practice has for the most part been replaced in commercial wine fermentation processes, that today rely instead upon the controlled production and use of pure or selectively mixed yeast strains. The pitching of beer in modern brewery operations is also carried out using carefully produced, high purity, pitching masses.

It has been proposed that commercial fermentation practices might next evolve to the point where immobilized cells could be routinely used. Some encapsulation methods employ organic solvents or other reagents that are strictly incompatible with many potential biological encapsulants.

The use of various gel-forming proteins (collagen and gelatine) and polysaccharides has resulted in the development of milder, more biocompatible immobilization techniques. Note, however, that in the case of agar and carrageenan, for example, such procedures can involve heating the polymer to a temperature where it is in a liquid state (e.g. up to 60 degrees C.), at which point the immobilizant is added, and whereafter the resulting mixture is solidified by cooling. The exposure of a biological immobilizant to the requisite elevated temperatures may be undesirable.

Gentler still is the simple gelation immobilization technique that was developed for and is used primarily with alginate. Generally, this technique involves the drop-wise addition of the ionic polysaccharide/immobilizant solution, through a syringe needle, into a solution of a divalent cation. The divalent ions cross-link various charged species on the polysaccharide molecule, with the result that insoluble gel beads are formed. Where alginate is selected as the ionic polysaccharide, as is typically the case, divalent calcium ions are employed as crosslinkers. This "syringe extrusion" process has the advantage of producing beads having a narrow, unimodal size distribution.

While it is known that yeast cells can be entrapped in calcium alginate and that the resulting immobilized yeast can be used in expediting fermentation processes, and while there are numerous references that are concerned with this advance, there are very few commercial applications.

There are a number of reasons for this. Alginate beads are very frangible, and their usefulness in commercial scale operations is therefore easily compromised. For example, being as they are so very soft, the beads are easily compressed. Commercial scale operations require large scale fermentation columns, such that in down-flow fermentations the beads are difficult to keep, from compacting, while in typical up-flow fermentations the beads are very prone to ablative wear and channelling.

Moreover, in the presence of, for example, citrates, lactates, and phosphates, alginate beads become prone to $Ca^{++}$ ion loss through chelation.

In commercial scale operations, the problem with alginate entrapment of cells also arises out of the manner in which the particulate gels are formed. The processes must be carried out at the production site where a yeast slurry and a solution of sodium alginate are mixed together. When this mixture is subsequently fed, dropwise, into a calcium salt solution, the sodium alginate is displaced as a calcium alginate salt gel, which over the course of the gelling process, occludes the suspended yeast cells within the gelling salt particles. Beads of uniform size and quality can be produced using this technique in conjunction with the above mentioned syringe extrusion process. Bead size, however, is limited by the syringe needle bore size and viscosity of the solution. As a result, beads of less than 3 mm, and especially beads of less than 1mm can be difficult to produce. At the same time, however, smaller diameter beads are needed to better facilitate both internal and external mass transfer, enhancing fermentation performance and minimizing bead rupture due to gas formation and accumulation. Production of small bead sizes has been attempted previously by modifying the syringe extrusion process, through the use of air jets impinging on the needle, electrostatic pulses, or vibrating needles.

The problem with unmodified alginate syringe extrusion bead production techniques that do not utilize one or another of these bead size reduction variations, is that economical production of immobilized beads is limited to large (3 mm to 5 mm) beads. The size of these large beads imposes diffusion limits on the transfer of substrate and product to and from the entrapped yeast cells. For example, in some cases the diffusion problems allow anaerobic fermentations to take place internally of the bead, notwithstanding the fact that to all outward appearances, aerobic fermentation is proceeding normally at or near the bead surface.

For large bead production (e.g. 3 mm) these can be formed by a single droplet generating technique, for which production rates may reach 24 l/h per syringe needle. Multiple needle extruders can even support small-scale industrial production rates.

On the other hand, while the variations on the syringe extrusion technique mentioned above can be employed for facilitating smaller alginate bead production, they too are-fraught with economic penalties. These include needle like extruders of one of two typical designs. The first such involves producing small drops of sodium alginate/yeast slurry, by passing the material through the needle, and with a vibratory action, shaking off a smaller drop than would otherwise form in the absence of the vibration. The second approach uses a coaxial flow needle, in which the solution of sodium alginate/yeast is passed through the centre of the needle, and as droplets form at the end of the needle, a coaxial flow of air pulls a small droplet away from the tip. These approaches can be used to keep alginate bead sizes as low as possible (with standard deviations of about 20%). However, the number of needles needed to maintain the flow rate is inversely proportional to the bead volume. Reducing the bead size to 500 micrometers or 100 micrometers requires the use of several hundreds or even hundreds of thousands of needles operating concurrently: a complex, expensive, and generally awkward solution. On the other hand, however, even these methodologies provide only very limited rates of bead production throughput, and are accordingly very difficult and expensive to scale up sufficiently to supply commercial fermentation processes.

Attempts have also been made to form more durable carrageenan beads utilizing the above "dropwise" methods. In the practice of this process, a type of carrageenan is employed, from which indigenous potassium ions have, been removed, (as for example, by way of ion exchange treatment). Droplets of this polymer are then extruded into a potassium ion-containing solution, to effect the gellation of the carrageenan beads. This method, however, results in the gel forming from the surface of the droplet, so that a gel membrane sets up around the droplet at first, and it is only as the salts diffuse inwardly through the ever thickening membrane, that the interior of the droplet gels up. As a consequence, the resulting gel structure of the bead that is formed in this manner is not as homogeneous as might be desired.

The production of beads by polymerizing emulsions in which droplets, comprising an aqueous suspension of a prepolymer and cell mixture, forms the discontinuous phase that is dispersed, using propeller type mixers to form the emulsion of droplets in a continuous oil phase, has also been attempted.

U.S. Pat. No. 5,079,011 teaches away from the use of alginate, citing the various short comings that are set out hereinabove. This U.S. Patent teaches instead, that a fibrillar matrix can be employed to immobilize the yeast cells, and cites the non-compressible nature of, for example, DEAE cellulose as demonstrative of its superiority to the weak physical structure that is associated with the aforementioned alginate. Note, however, that the immobilization of yeast cells in accordance with the materials promoted by the subject US patent, is limited to surface immobilization. This means that the amount of immobilized yeast is a function of bead surface area, and not of bead volume—and accordingly, that the reactor volume must be correspondingly larger (or the fermentation correspondingly slower). DEAE cellulose, moreover, is best suited for packed bed fermentations—it is not well suited to fluidized bed applications because the immobilized biomass is prone to detachment at the higher shear rates. Accordingly, DEAE cellulose surface immobilized yeast cells are not suited to primary fermentation in the production of beer, where the enhanced external mass transfer rates associated with fluidized bed reactors is desirable, if not necessary to commercial scale operations.

This latter problem also arises in prior art attempts to use carrageenan as a carrier. In Example 1 of PCT/US88/03980, the use of carrageenan beads is disclosed. Porous carrageenan beads having average diameters between 4.0 to 4.5 mm were obtained from Fisher Scientific and the yeast cells were then immobilized onto the bead surface, by way of incubation at 37 degrees C., for two hours in a shake flask.

An attempt to produce a carrageenan bead with yeast entrapped therein, using alginate bead production equipment, has not proven to be satisfactory. The alginate-bead producing equipment normally employed a rotatory disc atomizer to spray sodium alginate-containing droplets into a centrifugal bowl containing a suitable calcium salt. The alginate beads form in the bowl and the centrifugal rotation of the bowl carries the formed beads over the lip of the bowl, and into a collection vessel (typically the fermenter itself). When the equipment was utilized in the attempt to produce carrageenan beads, it was found that the viscosity of the carrageenan solutions that were sufficiently concentrated to avoid the mechanical problems associated with alginate beads, was much higher than the viscosity of the alginate solutions, (i.e., 2000 centipoise for the carrageenan versus 200 centipoise for alginate solutions). Accordingly, the alginate bead making equipment did not perform at all satisfactorily, either with respect to the bead quality or the size distribution of the resulting carrageenan beads.

Accordingly, there remains a need in the art for an economically practicable process that will enable physically durable carrageelnan beads of relatively small sizes to be produced with yeast cells entrapped therein.

SUMMARY OF THE INVENTION

In accordance with a broad aspect of the present invention, there is provided a process for immobilizing viable cells in polymer beads, for use in fermentation processes. The immobilization process comprises the steps of:

preparing an aqueous phase that is a mixture of either:
  a pre-polymeric molecular species; or,
  an ungelled polymeric molecular species; in an aqueous suspension of viable cells;

preparing a mixture of said aqueous phase and a food grade oil phase (i.e., one that is not substatially reactive with the other components in the bead forming milieu);

subjecting said mixture to shear by passing the same through a static mixer under flow-rate conditions selected to disperse the aqueous phase in the oil phase, such that aqueous phase droplets in a resulting emulsion have a desired droplet size distribution; and, subjecting the selected pre-polymeric or ungelled polymeric molecular species to polymerizing or gelling conditions (as the case may be), to thereby form polymer beads from the droplets, which have immobilized viable cells entrapped therein.

Preferably the present process is employed to immobilize yeast cells, for application in ethanolic fermentation processes.

Moreover, it is preferred that the beads be small, i.e., less than 3 mm; preferably less than 1.5 mm; and in particular, less than about 0.5 mm. In general, immobilized-yeast beads in the range of about 1.5 to about 0.2 mm, are preferred.

These immobilized cells are particularly useful in the conduct of carbohydrate fermentation processes for the production of ethanolic products. In general, malt beverages can be produced utilizing beads produced in accordance with the present invention. Malt beverages herein, includes brewery beverages, and fermented malt brewery beverages in particular. The general process of preparing fermented malt beverages, such as beer, ale, porter, malt liquor, low and non-alcoholic derivatives thereof, and other similar fermented alcoholic brewery beverages, hereinafter referred to simply as "beer" for convenience, is in general well known. As practiced in modern breweries, the process comprises, briefly, preparing a "mash" of malt, usually with cereal adjuncts, and heating the mash to solubilize the proteins and convert the starch into sugar and dextrins. The insoluble grains are filtered off and washed with hot water which is combined with the soluble material and the resulting wort boiled in a brew kettle to inactivate enzymes, sterilize the wort, extract desired hop components from added hops, and coagulate certain protein-like substances. The wort is then strained to remove spent hops and coagulate, cooled and pitched with yeast, and then fermented. The fermented, unmatured brew known as "green" or "ruh" beer is then "finished", aged—which is sometimes referred to as "lagering" and clarified, filtered, and then carbonated to produce the desired beer.

The pre-polymeric molecular species, or ungelled molecular species, as the case may be, is, for example, alginate, gellan gum, agar, polymerizable isocyanates (polyurethane), or carrageenan.

Alginate, however, is not the most preferred ungelled polymer in accordance with the present invention for the reasons already of record herein.

According to another aspect of the present invention, therefore, there is provided a process for immobilizing viable cells in generally spherical carrageenan-bead carriers. Such a process comprises preparing a mixture including:

i) an aqueous phase that is a mixture of a gellable concentration of un-gelled carrageenan, in an aqueous suspension of those viable cells, wherein the potassium concentration in the mixture is low enough that the thermogellation temperature of the carrageenan in the suspension is below a temperature to which the viable cells are substantially thermosensitive; and, ii) a food grade, non-reactive oil phase, at a first processing temperature that exceeds the thermogellation temperature of the carrageenan in that aqueous suspension, but which is below the temperature to which said cells are substantially thermosensitive.

That mixture is then subjected to shear by passing the same through a static mixer under flow-rate conditions selected to disperse the aqueous phase in the oil phase, such that a resulting emulsion has a droplet size distribution which, for a given static mixer, is a function of the selected flow rate. For the present purposes, a static mixer is a device that comprises a series of stationary elements that are arranged in longitudinally extending relation along a length of mixture conducting conduit. These elements form a plurality of intersecting channels that subdivide, rearrange, and recombine the flow of the mixture through that portion of the conduit, to form smaller and smaller layers within the flow, ideally until a single, generally homogenous stream exits the mixer.

The temperature of the resulting emulsion is then decreased from the above mentioned first processing temperature, to a second process temperature which is below the thermogellation temperature of the carrageenan in the suspension, to thereby form gel beads having immobilized viable cells entrapped therein.

In accordance with a particularly preferred practice according to the present invention, kappa-carrageenan is employed. kappa-carrageenan is a polysaccharide extracted from seaweeds. It consists of D-galactose 4-sulphate and 3,6-anhydro-D-galactose units. In an especially preferred practice under the present invention, a particular grade of kappa-carrageenan is used—which is commercially available as catalog designation X0909 from Copenhagen Pectin. A similar material is made commercially available under the catalog designation of NJAL 798, from FMC Corporation. This product is particularly suited to immobilization of cells—and does not gel at room temperature unless potassium ions are added.

DETAILED DESCRIPTION OF THE INVENTION

INTRODUCTION TO THE DRAWINGS

Figure 1:
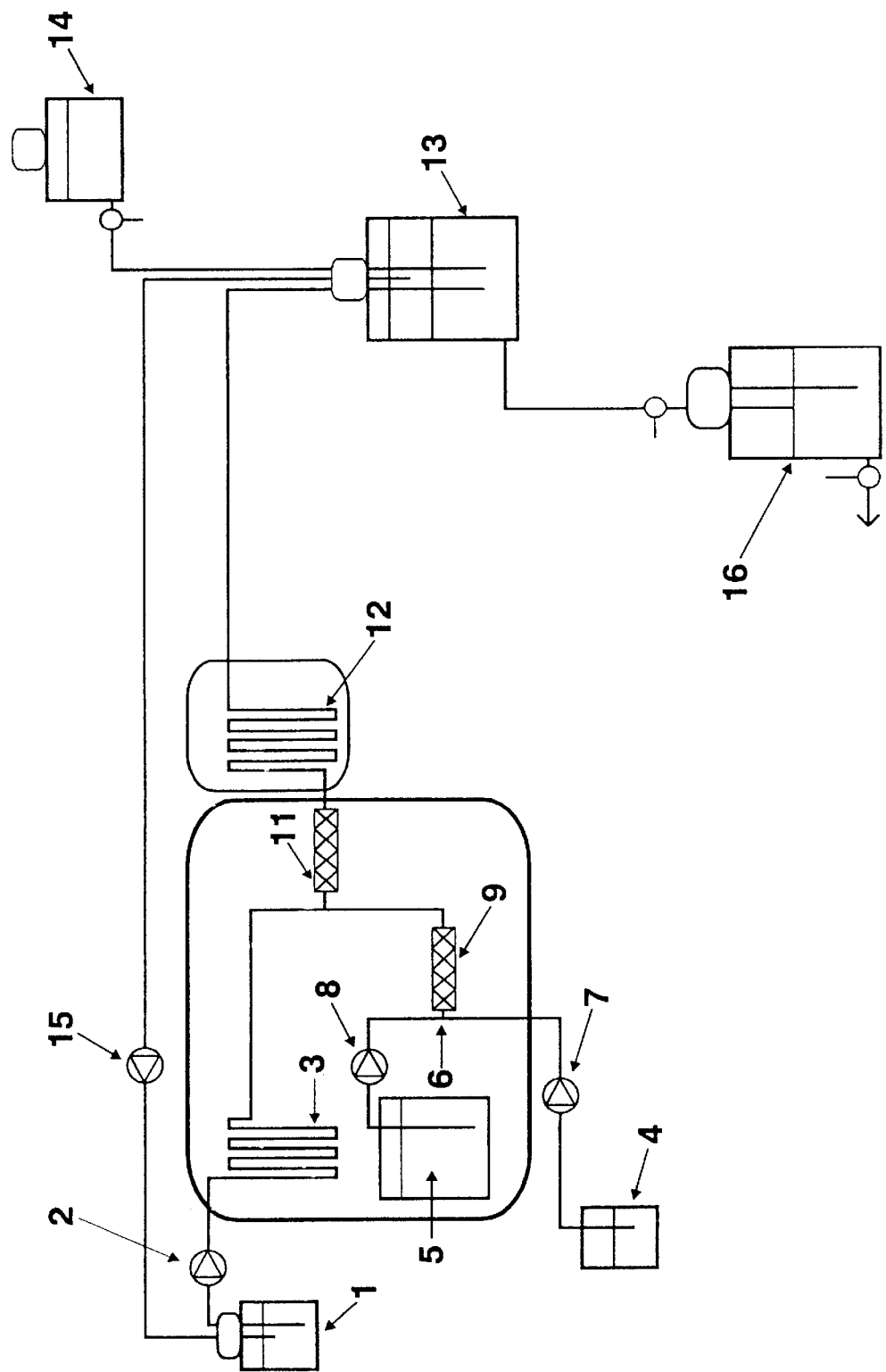
Figure 2:
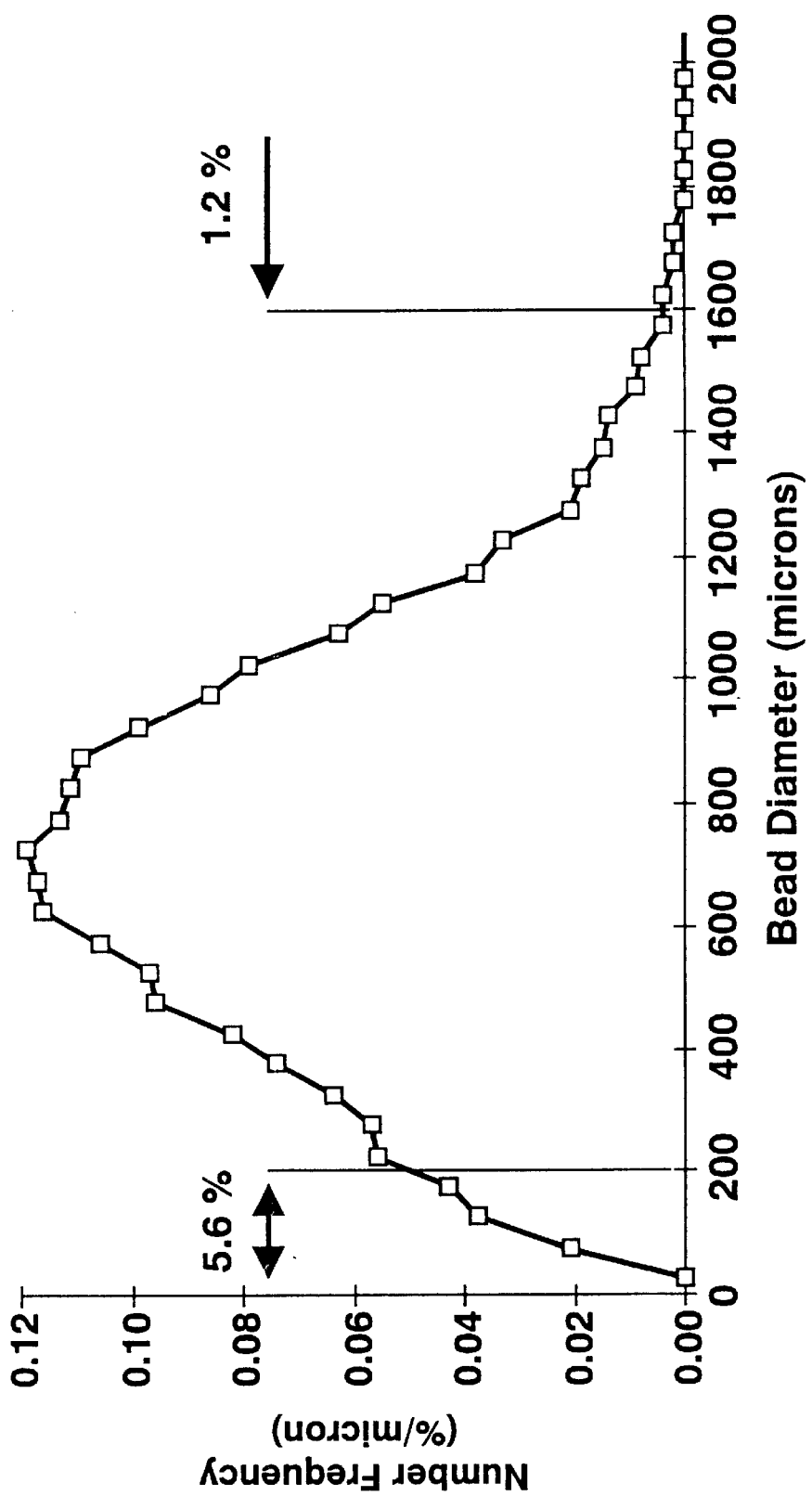
Figure 3:
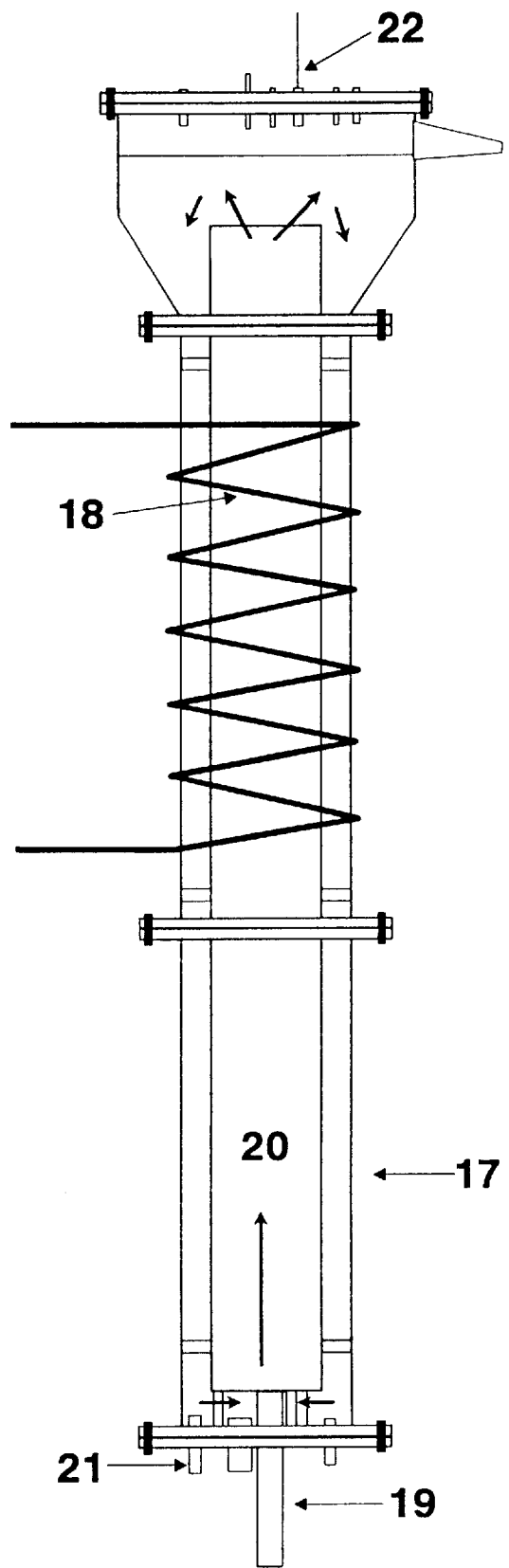

FIG. 1 is a schematic representation of a process according to the present invention, for producing carrageenan encapsulated yeast beads; and, FIG. 2 is a graphic representation showing the size distribution of a lot of beads produced in accordance with the process as outlined in FIG. 1; and, FIG. 3 is a schematic representation of a gas-lift fluidized bed bioreactor employing beads produced in accordance with the process as illustrated in FIG. 1.

EXAMPLE 1

In accordance with one aspect of the present invention, there is provided a process for the production of carrageenan immobilized yeast beads for use in beverage fermentation processes.

A K-carrageenan polymer (specification X-0909—from Copenhagen Pectin, Denmark), was dissolved (at 80° C., and a concentration of 30 grams per liter) in distilled water containing 1.5 grams per liter of potassium chloride (KCl) In aqueous solutions of this polymer, the gelation temperature is a function of the potassium ion concentration—and in the specific case of the above the 1:20 by weight ratio of KCl to polymer was selected so that the gelation temperature would be about 28° C. The actual mixing of the solution was carried out in a 40 liter bioreactor, in which the solution was held at 80° C. for about 20 minutes, in order to ensure that all of the polymer was properly solubilized.

The solution was then sterilized by heating to 121° C. for one hour, then allowed to cool down to 40° C. under 1.7 atmospheres pressure, in preparation for use in the production of the above mentioned beads.

A commercial grade canola oil (obtained from Pasquale Bros. Inc. Canada), was also sterilized by heating to 121° C. for one hour, and then cooled and transferred to a heat exchanger to adjust the temperature as necessary to about 40° C.

An aqueous phase for dispersion in the canola oil, was then prepared by mixing a yeast inoculum into the pre-polymeric, potassium-containing solution of K-carrageenan. To this end, a yeast slurry was heated from about room temperature (i.e., 20° C.) to about 40° C., and the actual mixing of the inoculum slurry and the un-gelled carrageenan solution was then carried out by passing the inoculum and the un-gelled solution through a static mixer together. The static mixer employed for this purpose was a model G-04667-04 static mixer obtained from Cole Parmer Instrument Company, USA. The mixer is a 12 element mixer having a diameter of 6.4 mm.

The inoculated ungelled aqueous phase was then immediately mixed, using another static mixer, with the oil phase that had been prepared in the manner set out above. This second static mixer was a model G-04667-08 static mixer, (as obtained from Cole Parmer Instrument Company, USA), which is a 12 element, 12.7 mm diameter static mixer.

On exiting the second mixer, the resulting emulsion was immediately cooled down to about 5° C., in a heat exchanger. This precipitated the gelation of the K-carrageenan. The emulsion containing the incipiently gelled or gelling beads was then passed into a sterile 22 gram per liter solution of KCl, that wRas contained in an oil separation tank. The incipient beads were further hardened by this immersion into the KCl solution, and the oil phase was separated out and decanted, and reused in the process in the manner described above.

The gelled polymer beads were transferred then into a tank, from which an airlift bio-reactor can be loaded, on an "as needed" basis Referring now to FIG. 1 of the appended drawings, there is shown a schematic representation of the process as carried out in relation to Example 1, as set forth above.

The sterilized commercial grade canola oil was transferred from a holding tank 1, by way of peristaltic pump 2, through to heat exchanger 3. On exiting heat exchanger 3, the temperature of the oil was about 40° C.

The yeast inoculum contained in tank 4 at 40° C., and the ungelled carrageenan polymer solution in tank 5 (also at 40° C., were pumped together through a junction manifold 6 (a simple "T" junction in the respective lines leading from each of the above mentioned tanks), by peristaltic pumps 7 and 8. Manifold 6 is connected at the input side of a first static mixer 9, in which the inoculum and the un-gelled carrageenan solution were mixed to provide an aqueous phase.

This aqueous phase and the oil phase are then introduced together, through manifold 10, into a second static mixer, 11.

The emulsion that is produced in the static mixer 11 is then passed through a heat exchanger 12, in which the temperature is reduced to below the gelation temperature for the carrageenan. The newly formed beads, still suspended in the cooled oil, are then passed along to a separation tank 13.

Separation tank 13 is supplied with a KCl solution that is held in tank 14. Oil rises to the top of separation tank 13, while the hardening beads become suspended in the KCl solution that is delivered from tank 14. The oil is then decanted, and pumped by pump 15, for re-use. The beads, suspended in the KCl solution, are then pumped to a holding tank 16, from which they are withdrawn as required for loading a bio-reactor, (such as that which is depicted in FIG. 3).

EXAMPLE 2

In accordance with another aspect of the present invention, there is provided a process for the production of beer in a gas-lift bio-reactor.

Immobilized yeast cell beads were prepared substantially as described in Example 1. The yeast strain was a commercial lager yeast obtained from the Labatt Culture Collection. The beads had a mean diameter of about 1 mm, and a coefficient of variation of about 40%. The beads were acclimated in a nutrient medium that consisted of 16° Plato beer wort.

A gas-lift bio-reactor 17 (having a nominal working volume of about 50 liters), was utilized in carrying out a primary beer fermentation process. The reactor was insulated to manage ambient heat loss, and a thermal glycol jacket 18 was included to provide temperature control as needed.

$$\text{SPARGING RATE} = \frac{\text{GAS VOLUME}}{\text{LIQUID VOLUME} \times \text{TIME}}$$

The reactor was sparged at a rate (as defined above) of 0.03, by passing an air/$CO_2$ mixture through a sparger 19, into the reactor's draft tube 20. The sparge gas mixture comprised: 98% $CO_2$, and 2% air.

The reactor was equipped with dissolved oxygen and pH probes, (not shown). Over the course of most of the fermentation, the dissolved oxygen concentration fell to near zero. This is believed to reflect a situation in which substantially all of the oxygen that is introduced during the fermentation process is utilized immediately by the yeast cells.

Beer wort was introduced at the base 21 of the bioreactor 17. The fermentation was carried to completion (ie substantially all of the fermentable wort sugars were consumed) in about 22 hours. This compares with a classical fermentation process in which fermentation does not normally reach completion until fully six or seven days have passed. Green (i.e., unmatured beer), fermented beer was drawn off from the top of the column, and contained about $10^7$ cells per milliliter—which is generally the equivalent to the amount of concentration of yeast cells that are present in conventionally brewed beers.

In accordance with this aspect of the present invention, the conduct of the brewing process in general, and in which no substantial excess of oxygen is supplied to the fermenting yeasts, and in which the proportion of biomass production is generally equal to the biomass production that is occasioned in the production of a corresponding, conventionally brewed beer, is believed to result in the production of a beer using immobilized cells as aforesaid, that exhibits a flavor profile that approximates that of a comparable, conventionally brewed beer. Table 1 sets out analytical results for a comparison between such a conventionally brewed beer, and a beer brewed in accordance with the present invention, in which an immobilized cell fermentation is carried out.

| ANALYSIS | IMMOBILIZED CELL FERMENTATION | CONVENTIONAL FERMENTATION |
|---|---|---|
| Ethanol (% w/v) | 5.09 | 5.00 |
| Foam (seconds) | 150 | 180 |
| Protein (%) | .029 | .031 |
| Colour (SRM) | 2.4 | 3.0 |
| Bitterness (BE) | 9.5 | 12 |
| pH | 4.06 | 4.1 |
| Diacetyl (ppm) | 15 | less than 20 |
| DMS (ppb) | 43 | less than 70 |
| Acetaldehyde (ppm) | 8 | 4.9 |
| Ethyl Acetate (ppm) | 11.3 | 26.4 |
| Propanol (ppm) | 32.5 | 9.9 |
| Isobutanol (ppm) | 11.1 | 7.8 |
| isoamyl alcohol (ppm) | 47.4 | 46.7 |
| isoamyl acetate (ppm) | 0 | .08 |

Taste panel analysis judged that an "immobilized" beer prepared in accordance with the present invention, was similar to otherwise comparable, conventionally brewed beer.

EXAMPLE 3

In accordance with yet another aspect of the present invention, there is provided a process for the production of neutral ethanolic solutions in accordance with which the beads are produced in the manner set out in Example 1. The bio-reactor apparatus is identical to that employed in Example 2.

The fermentable substrate, however, was a high maltose corn syrup containing about 14% fermentable sugars. The syrup was fermented on an "as is" basis, although various nitrogenous and mineral nutrient supplements could be added as and when required over the course of the fermentation Residence time for fermentation was about 25 hours, to completion, with the fermented solution reaching an ethanol content of about 7% v/v.

The fermented solution had a very neutral flavour.

EXAMPLE 4

In accordance with still another aspect of the present invention, it is proposed that alginate beads could be produced in the manner specified below.

Sodium alginate solution having a concentration in the range of 1 to 4% (w/v), was prepared, by dissolving the alginate salt in distilled water.

An aqueous phase was then prepared by mixing a yeast inoculum into the ungelled, alginate solution. To this end, a yeast slurry was prepared and mixed with the pre-polymeric alginate solution, by passing the inoculum and the ungelled solution together through a static mixer. A suitable static mixer for this purpose would be the model G-04667-04 static mixer obtained from Cole Parmer Instrument Company, USA, as mentioned above in Example 1. As mentioned above, that mixer is a 12 element mixer having a diameter of 6.4 mm.

A 20% calcium citrate solution is then added to complete the aqueous phase (5%v/v).

The resulting inoculated, un-gelled aqueous phase would then be emulsified, using another static mixer, into a continuous oil phase. Also as per Example 1, this second static mixer could be a model G-04667-08 static mixer (also as obtained from Cole Parnier Instrument Company, USA) which is a 12 element, 12.7 mm diameter static mixer.

On exiting the second mixer, the resulting emulsion would then be mixed with an oil containing an acid, such as glacial acetic acid. The amount of acid used in this step is proportional to the amount of reduction in pH that is necessary to induce the polymerization reaction in the solubilized alginate that is contained in the discontinuous aqueous phase. Note, however, that the use of alginate in this context is not preferred as compared with carageenan—because the addition of the requisite amounts of acid can compromise the viability of the cells being immobilized.

In the present circumstances, the added oil should contain 0.5 ml of glacial acetic acid for every 20 ml of alginate in the discontinuous phase. As the pH of the discontinuous phase drops in the resulting emulsion, calcium ions are released from the citrate complex, and recombine with the alginate to form calcium alginate polymer gel beads, with the yeast cells entrapped therein. The emulsion containing the beads would then be passed into a phase separation tank in which the oil phase would be separated out and decanted.

The beads would then be transferred into a holding tank, from which a gas-lift bio-reactor could be loaded, on an "as needed" basis.

We claim:

1. In a process for immobilizing viable yeast cells in polymer beads for use in a malt beverage fermentation process, the improvement that comprises the steps of:

preparing a first mixture by mixing an aqueous solution of a molecular species selected from the group consisting of:

alginate; gellan gum; agar; polymerizable isocyanates; and carrageenan;

with an aqueous suspension of viable yeast cells in a first static mixer;

preparing a second mixture of said first mixture and a non-reactive food-grade oil phase;

subjecting said second mixture to shear by passing said second mixture through a second static mixer under flow-rate conditions selected to disperse the first mixture in the oil phase, such that first mixture droplets in a resulting emulsion have a desired droplet size distribution;

subjecting said selected molecular species to corresponding gelling or polymerizing conditions to thereby form polymer beads from said droplets, whereby said beads have immobilized viable yeast cells entrapped therein; and separating said beads from said non-reactive food-grade oil.

2. The process according to claim 1 wherein said beads have a mean diameter less than 3 mm.

3. The process according to claim 2 wherein said beads have a mean diameter about 1.5 mm to about 0.2 mm.

4. The process according to claim 1 wherein the molecular species is carrageenan.

5. The process according to claim 4 wherein the carrageenan is K-carrageenan.

6. The process according to claim 3 wherein the non-reactive food-grade oil is canola oil.

7. A process for immobilizing viable yeast cells in K-carrageenan beads for use in a beer fermentation process, comprising the steps of:

preparing a first mixture by mixing an aqueous solution of K-carrageenan with an aqueous suspension of viable yeast cells in a first static mixer;

preparing a second mixture of said first mixture and a canola oil phase;

subjecting said second mixture to shear by passing said second mixture through a second static mixer under flow-rate conditions selected to disperse the first mixture in the canola oil phase, such that first mixture droplets in a resulting emulsion have a desired droplet size distribution;

subjecting said K-carrageenan to gelling conditions to thereby form polymer beads from said droplets, whereby said beads have immobilized viable yeast cells entrapped therein; and separating said beads from said canola oil.

* * * * *